United States Patent

Shibasaki et al.

[11] Patent Number: 6,084,123
[45] Date of Patent: Jul. 4, 2000

[54] PROCESS FOR THE PREPARATION OF OPTICALLY ACTIVE 1-AMINOPHOSPHONIC ACID DERIVATIVES AND NOVEL PHOSPHONATE COMPOUNDS

[75] Inventors: Masakatsu Shibasaki, Mitaka; Hiroaki Sasai, Kawanishi; Yoshihiro Tahara, Sagamihara, all of Japan

[73] Assignee: Hokko Chemical Industry Co., Ltd., Tokyo, Japan

[21] Appl. No.: 09/043,678

[22] PCT Filed: Sep. 26, 1996

[86] PCT No.: PCT/JP96/02794

§ 371 Date: May 20, 1998

§ 102(e) Date: May 20, 1998

[87] PCT Pub. No.: WO97/11954

PCT Pub. Date: Apr. 3, 1997

[30] Foreign Application Priority Data

Sep. 26, 1995 [JP] Japan ................................. 7-248044

[51] Int. Cl.$^7$ .................................................... C07F 9/44
[52] U.S. Cl. ............................................. 562/16; 562/11
[58] Field of Search ......................................... 562/11, 16

[56] References Cited

U.S. PATENT DOCUMENTS

| | | |
|---|---|---|
| 4,098,849 | 7/1978 | Redmore . |
| 4,235,809 | 11/1980 | Redmore . |
| 4,442,286 | 4/1984 | Redmore . |
| 4,804,500 | 2/1989 | Miller . |

FOREIGN PATENT DOCUMENTS

| | | |
|---|---|---|
| 0540437A1 | 5/1993 | France . |
| 5-222701 | 8/1993 | Japan . |
| 6-154618 | 6/1994 | Japan . |

OTHER PUBLICATIONS

"Catalytic Asymmteric Synthesis of $^{\alpha-Amino}$ Phosphonates Using Lanthanoid–Potassium–BINOL Complexes", by H. Sasai et al., J. Org. Chem., vol. 60, No. 21, Oct. 20, 1995, pp. 6656–6657.

"Synthesis of 1–aminoalkane phosponic acids via benzhydrylic Schiff bases" by I. Kurt, et al., Chemical Abstracts 96:104372w vol. 96, 1992 p. 721.

*Primary Examiner*—Pual J. Killos
*Assistant Examiner*—Jean F Vollano
*Attorney, Agent, or Firm*—Birch, Stewart, Kolasch & Birch, LLP

[57] ABSTRACT

Provided is a process for the preparation of an optically active (R)- or (S)-1-aminophosphonic acid derivative of the general formula (Ia) or (Ib) given below, which process comprises reacting an amino-protected imine having general formula (II): $R^1$—N=CHR$^2$ where $R^1$ is diphenylmethyl group or the like and $R^2$ is an alkyl group or the like, with a phosphonic acid ester in the presence of an asymmetric catalyst consisting of a rare earth element-alkali metal-binaphthol complex, to produce an (R)- or (S)-N-protected-1-aminophosphonate compound, and then subjecting the phosphonate compound to catalytic reduction with hydrogen and to acidic hydrolysis.

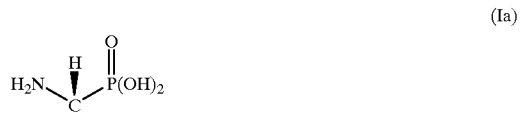

(Ia)

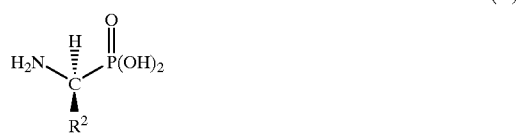

(Ib)

There are also provided novel intermediates, and a process of preparing an asymmetric catalyst consisting of a rare element-alkali metal-binaphthol complex.

3 Claims, 1 Drawing Sheet

PROCESS FOR THE PREPARATION OF OPTICALLY ACTIVE 1-AMINOPHOSPHONIC ACID DERIVATIVES AND NOVEL PHOSPHONATE COMPOUNDS

This application is the national phase under 35 U.S.C. §371 of prior PCT International Application No., PCT/JP 96/02794, which has an International filing date of Sep. 26, 1996, which designated the United States of America, the entire contents of which are hereby incorporated by reference.

TECHNICAL FIELD

This invention relates to a process for the preparation of an optically active 1-aminophosphonic acid derivative with using a catalyst for asymmetric synthesis of said derivative. This invention also relates to a method for the preparation of a novel catalyst for use in an asymmetric synthesis in the above process. Furthermore, this invention includes also a novel 1-aminophosphonate derivative obtained as intermediates in the above process.

BACKGROUND ART

It is known that a 1-aminoalkylphosphonic acid or its peptide-related derivatives have an antibacterial action against gram-positive bacteria and gram-negative bacteria and also can enhance the activity of some antibiotics such as penicillin, cephalosporin and D-cycloserine, that alaphospharine, which is a dipeptide obtained from L-alanine and L-aminoethylphosphonic acid, is especially important, and that in general, an optically active 1-aminoalkylphosphonic acid derivative and particularly its derivatives in the L-form (R-form) thereof can exhibit broad biological activities (Japanese patent application first publication "Kokai" No. 61-88895).

Such a process for obtaining the optically active 1-aminoalkylphosphonic acid, which comprise effecting an asymmetric synthesis thereof with using an enzyme, include methods described in the "Tetrahedron Asymmetry" Vol.4, p.1965 (1993) and Japanese patent application first publication "Kokai" No. 61-88895 and others.

For example, Japanese patent application first publication "Kokai" No. 61-88895 describes such a process for the preparation of an optically active stereoisomer of 1-aminoalkylphosphonic acid of the formula:

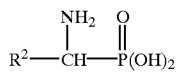

(A)

where $R^2$ represents, for example, a branched or preferably straight alkyl group of 1 to 6 carbon atoms, particularly 1 to 4 carbon atoms and optionally substituted with a halogen, hydroxyl group, alkoxy group of 1 to 3 carbon atoms, phenyl group and/or phenoxy group, or alternatively $R^2$ represents a phenyl group, which process comprises effecting the optical resolution of the N-acyl derivative of a 1-aminoalkylphosphonic acid or a racemic mixture of the 1-aminoalkyl phosphonic acid with use of an enzyme, and then deacylating the resulting optically active N-acyl derivative to prepare the stereo-isomer, characterized in that the enzymatic, optical resolution is effected with penicillin-G-amidase. However, this enzymatic and asymmetric synthetic process has a problem that a scope of the substrate which can be used as the starting material is limited.

Furthermore, as such a process for preparation of the optically active 1-aminoalkylphosphonic acid which comprises effecting the asymmetric synthesis thereof without using the enzyme, there are hitherto known several processes which are described in the following literatures (1) to (4). Thus;

(1) there is known a process for effecting the optical resolution of a racemic mixture of 1-aminoalkylphosphonic acid with using anhydrous dibenzoyl-L-tartaric acid, wherein the target optically active α-aminoalkylphosphonic acid is obtained in a yield of 70 to 87% (Canadian Journal of Chemical Engineering, Vol.61, p.2425, 1983);

(2) there is known a process for the preparation of optically active 1-aminoalkylphosphonic acid which comprises effecting asymmetric alkylation to give an optically active aminoalkylphosphonic acid ester, wherein the target substance is obtained in a yield of 50 to 86% and at an optical purity of 25 to 76% (Tetrahedron Letters, Vol.33, p.6127, 1992);

(3) there is known a process for the preparation of optically active 1-aminoalkylphosphonic acid which comprises effecting a diastereo-selective addition reaction of phosphonic acid ester to an optically active imine, wherein the target substance is obtained in a yield of 30 to 90% and at an optical purity of 71 to 99% (The Journal of American Chemical Society, Vol.116, p.9377, 1994); and (4) there is known a process for the preparation of optically active α-aminoalkylphosphonic acid which comprises effecting an asymmetric hydrogenation reaction of an olefinic derivative of said compound with using an asymmetric catalyst, wherein the target substance is obtained in a yield of 92% and at an optical purity of 63 to 96% (Synthetic Communications, Vol.26, p.777, 1996).

However, the process described in the literature (1) has a problem that a number of the reaction steps are required and the operation of the process is complicated. The processes described in the literatures (2) and (3) have a problem that the optically active starting material is required to be used in a stoichiometric amount, and so on. Furthermore, the process described in the literature (4) has a problem that a number of the reaction steps are required in order to prepare the olefinic derivative which is a starting material and also that the nature of the starting material is limited. Hence, these above-mentioned prior art processes are not advantageous industrially.

For these reasons, there is an outstanding demand seeking for such a novel process for the preparation of the optically active 1-amino-phosphonic acid derivative, by which it is feasible to prepare a large amount of the optically active compound even with using a small amount of an asymmetric compound as the starting resource, and by which the optically active compound can be obtained by shorter steps of the reaction, as compared with the prior art processes. In addition, there is also a demand seeking for such a novel catalyst available for the asymmetric synthesis of said derivative, as well as a novel 1-aminophosphonate compound obtainable by said process.

Furthermore, the "Liebich Annalen der Chemie", pp.1153–1155 (1990) describes a non-asymmetric synthetic process for the preparation of a compound of the general formula:

where $R^1$ stands for styryl group or the like, which comprises reacting N,N'-alkylidene bis-amide of the general formula:

where R$^1$ stands for styryl group or the like and R$^2$ stands for an alkylidene group, with PCl$_3$ and acetic acid at 60 to 80° C. for one hour and thereafter hydrolyzing the resulting reaction product to prepare the target compound in a yield of 39 to 99%.

Besides, Japanese patent application first publn. Kokai No. Hei-6-154618 describes, as a catalyst for use in an asymmetric nitroaldol reaction which comprises reacting an aldehyde compound with nitromethane, the following two catalysts:

(1) a catalyst for use in the asymmetric synthesis, which has been prepared from a dialkali-metal salt of optically active 2,2'-dihydroxy-1,1'-binaphthyl, namely 1,1'-bi-2-naphthol of the formula (A$_R$) or (A$_S$):

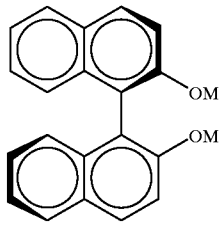

(A$_R$)

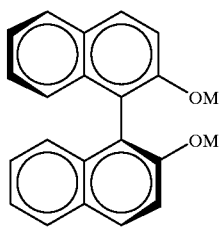

(A$_S$)

where M is Li, K or Na;

a lanthanum compound of the formula: LaX$_3$ where X is F, Cl, Br, I, NO$_3$ or CH$_3$CO$_2$; and an alkali metal alkoxide or alkali metal hydroxide of the formula: MOR or MOH where M is Li, K or Na and R is isopropyl or t-butyl group, in the presence of an aqueous solvent; and (2) a catalyst for use in the asymmetric synthesis, which contains such active species as obtained by reacting optically active 2,2'-dihydroxy-1,1'-binaphthyl, namely 1,1'-bi-2-naphthol of the formula (B$_R$) or (B$_S$):

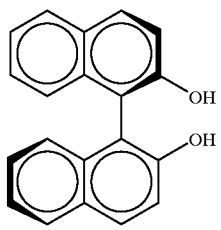

(B$_R$)

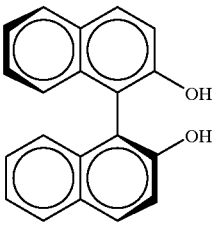

(B$_S$)

with a lanthanum alkoxide of the formula: La(OR)$_3$ where R is an isopropyl or t-butyl group, in an ether-type organic solvent, and which catalyst is used characteristically in the presence of lithium chloride and an aqueous solvent.

DISCLOSURE OF THE INVENTION

It is an object of this invention to solve the problems attendant upon the prior arts as described above. Particularly, an object of this invention is to provide a novel process for the preparation of an optically active 1-aminophosphonic acid derivative, which is able to prepare the optically active 1-aminophosphonic acid derivative in good yields even with using a small amount of an optically active starting material and a small number of reaction steps and with making facile operation of the process.

Further, it is a further object of this invention to provide a method for the preparation of such a novel catalyst for use in said asymmetric synthesis, which can be used in the production of the optically active 1-aminophosphonic acid derivative.

Furthermore, it is another object of this invention to provide such a novel optically active 1-amino-phosphonate derivative which can preferably be used for the preparation of the optically active 1-aminophosphonic acid derivative.

The present inventors have eagerly made extensive investigations in order to achieve the above-mentioned objects. As a result, the present inventors have now found that when a reaction between an alkoxide of a rare earth element (referred to also as the rare earth metal) such as lanthanum, (R)-2,2'-dihydroxy-1,1'-binaphthyl (namely, (R)-(+)-1,1'-bi-2-naphthol) or (S)-2,2'-dihydroxy-1,1'-binaphthyl (namely, (S)-(−)-1,1'-bi-2-naphthol) (hereinafter, these two binaphthyl compounds are sometime abbreviated simply as "binaphthol") and an alkali metal compound (which may be alkyl lithium, bis(trimethylsilyl) potassium amide or alkali metal (Na, K or Li) alkoxide) is conducted in such proportions of these reactant compound that the molar ratio of the binaphthol, the rare earth element alkoxide and the alkali metal compound is in a range of 1~10:1:1~10, preferably in a range of 1~3:1:1~3, and when said reaction is conducted under an atmosphere of an inactive gas and in an organic solvent (which may be aqueous) such as tetrahydrofuran or ethyl ether in accordance with the procedure as described hereinafter, there can be prepared as the resulting reaction product such a complex compound which consists of said rare earth element with the binaphthol and said alkali metal; and also that said complex compound is able to act as an asymmetric catalyst when said complex compound is employed as a catalyst upon conducting a reaction of an imine of the formula:

R$^1$—N=CHR$^2$ where R$^1$ denotes diphenylmethyl group or the like and R$^2$ denotes an alkyl group or the like, with an alkyl ester or another ester of phosphonic acid in order to prepare a phosphonic acid ester which bears a substituted or unsubstituted amino group at the 1-position thereof and which is represented by the formula (VI):

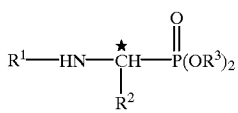
(IV)

where $R^1$ and $R^2$ have the same meanings as defined above, $R^3$ stands for an ester-forming group such as alkyl group and the symbol * stands for an asymmetric carbon atom, and further that, with the aforesaid complex compound acting as the asymmetric catalyst, it is feasible to produce preferentially either one of the (R)-enantiomer and (S)-enantiomer of the compound of the formula (IV) in a remarkably higher yield than the yield of the other enantiomer.

The above-mentioned complex compound consisting of the rare earth element, binaphthol and the alkali metal has been obtained as the reaction product which is prepared by reacting in the organic solvent and under the inactive gas atmosphere the rare element alkoxide with binaphthol and the alkali metal compound chosen from an alkylated lithium, bis(tri-methylsily) potassium amide and an alkali metal alkoxide in the above-mentioned proportions of these reactants, and said complex compound is hereinafter sometime abbreviated as "rare element-alkali metal-binaphthol complex", though said complex compound is presumed with a high certainty to have a such a chemical structure described hereinafter.

According to a first aspect of this invention, therefore, there is provided a process for the preparation of an optically active (R) or (S)-1-aminophosphonic acid derivative represented by the general formula (Ia) or (Ib):

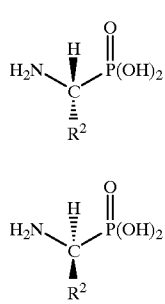

(Ia)

(Ib)

wherein $R^2$ has the same meaning as given below, characterized in that the process comprises the steps:

reacting an imine represented by the general formula (II):

$$R^1-N=CHR^2 \qquad (II)$$

wherein $R^1$ stands for diphenylmethyl group or an alkoxyphenyl group and $R^2$ stands for an alkyl group or a cycloalkyl group, or an aryl group-containing hydrocarbon radical, or $R^2$ stands for an aryl group optionally substituted with a halogen atom or an alkoxy group, with a phosphonic acid ester represented by the general formula (III):

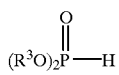
(III)

wherein $R^3$ stands for an alkyl group, a cycloalkyl group, allyl group or an aryl group or an aryl group-containing hydrocarbon radical, in the presence of an asymmetric catalyst consisting of a rare earth element-alkali metal-binaphthol complex to produce an (R)- or (S)-N-protected-1-amino-phosphonate compound represented by the general formula (IVa) or (IVb):

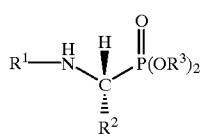
(IVa)

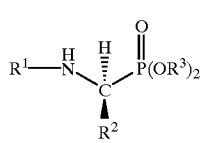
(IVb)

wherein $R^1$, $R^2$ and $R^3$ have the same meanings as defined above;

subjecting the compound of the formula (IVa) or (IVb) to catalytic reduction with hydrogen to eliminate the amino-protecting group $R^1$ therefrom to produce a (R)- or (S)-1-amino-phosphonic acid ester represented by the formula (Ia') or (Ib'):

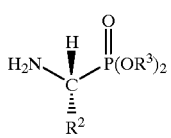
(Ia')

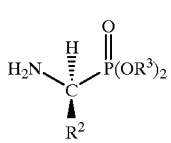
(Ib')

wherein $R^3$ has the same meaning as defined above, and subjecting the resulting compound of the formula (Ia') or (Ib') to acidic hydrolysis to eliminate the ester-forming group $R^3$ therefrom.

The process of the first aspect of this invention will be further described hereinafter.

The rare earth element contained in the rare earth element-alkali metal-binaphthol complex used as the asymmetric catalyst in the process of the first aspect of this invention is selected from scandium, yttrium, lanthanum, cerium, praseodymium, neodymium, promethium, samarium, europium, gadolinium, terbium, dysprosium, holmium, erbium, thulium, ytterbium and lutetium. Furthermore, the alkali metal contained in the said complex is preferably sodium, potassium or lithium.

The above-mentioned rare earth element-alkali metal-binaphthol complex used as the asymmetric catalyst has been presumed with a high probability to be such a complex having the chemical structure represented by the formula (a):

(a)

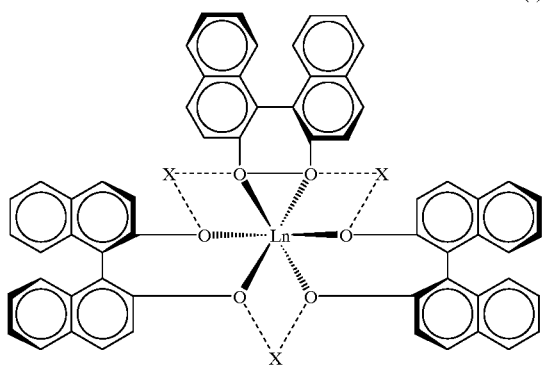

when the binaphthol component contained in the complex is (R)-(+)-1,1'-bi-2-naphthol. While, the rare earth element-alkali metal-binaphthol complex has been presumed with a high probability to be such a complex having the chemical structure represented by the formula (b):

(b)

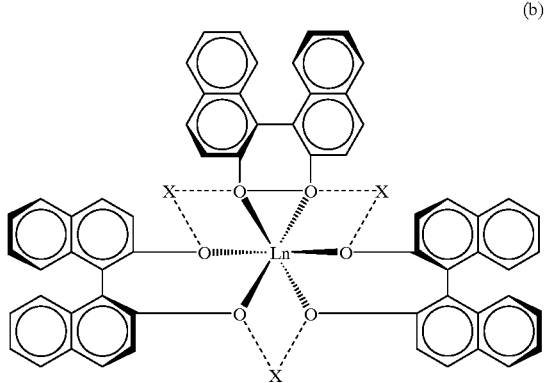

when the binaphthol component is (S)-(-)-1,1'-bi-2-naphthol. In the formulas (a) and (b) shown above, Ln stands for the rare earth element (namely, a rare earth metal atom) and X stands for an alkali metal atom.

The imine compound of the formula (II) used as the starting compound in the process of the first aspect of this invention is a known compound and can be prepared by the method hitherto known. For example, where $R^1$ in the formula (II) is the diphenylmethyl or alkoxyphenyl group, the imine compound can be prepared using diphenylmethyl amine or alkoxyphenyl amine as the starting material by the method described in Japanese patent application first publn. No. Kokai 62-289558 and others.

Where $R^1$ in the imine of the formula (II) is p-alkoxyphenyl group, an example of the alkoxy group, which is the substituent bound to the para-position of the benzene ring of said p-alkoxyphenyl group, includes methoxy group, ethoxy group, n-propoxy group, isopropoxy group, n-butoxy group, sec-butoxy group, t-butoxy group, isobutoxy group, isohexyloxy group and the like.

Where $R^2$ in the imine of the formula (II) is the alkyl group, such alkyl group includes those having 1 to 13 carbon atoms and may be of a straight or branched chain. An example of such alkyl group includes, for example, methyl group, ethyl group, n-propyl group, isopropyl group, n-butyl group, isobutyl group, tert-butyl group, n-pentyl group, isopentyl group, neopentyl group, dodecyl group, tridecyl group and the like.

Where $R^2$ in the imine of the formula (II) is the cycloalkyl group, an example of such cycloalkyl group includes particularly cyclopentyl group, cyclohexyl group and the like.

Where $R^2$ is the aryl group, an example of such aryl group includes particularly phenyl group, p-chlorophenyl group, p-fluoropheny group, p-methoxyphenyl group, tolyl group, xylyl group, naphthyl group and the like. The ring of the aryl group may optionally be substituted with a halogen atom or atom(s) such as chlorine, bromine, iodine and fluorine, as well as an alkoxy group or group(s) such as methoxy group, ethoxy group, n-propoxy group, isopropoxy group, n-butoxy group, sec-butoxy group, t-butoxy group, isohexyloxy group and the like.

Where $R^2$ in the imine of the formula (II) is the aryl group-containing hydrocarbon radical, an example of such aryl group-containing hydrocarbon radical includes an arylalkyl group such as benzyl group and phenethyl group; and an arylvinyl group such as (E)-styryl group and p-methylphenylvinyl group ($CH_3$—$C_6H_4$—$CH$=$CH$—).

Among such groups $R^2$, the alkyl group is most preferable, and among alkyl groups, ethyl group, n-propyl group, isopropyl group and n-butyl group are preferable.

Particular examples of the imine of the formula (II) include the followings.

Thus, N-ethylidene diphenylmethylamine is used as the imine of the formula (II). Besides, it is possible to use such a compound where the ethylidene group in the above-mentioned N-ethylidene diphenylmethylamine has been replaced by propylidene group, butylidene group, 2-methylpropylidene group, pentylidene group, 3-methylbutylidene group, neopentylidene group, hexylidene group, 4-methylpentylidene group, neohexylidene group, tridecylidene group, tetradecylidene group, cyclopentylmethylidene group, cyclohexylmethylidene group, phenylmethylidene group, p-chlorophenylmethylidene group, p-fluorophenylmethylidene group, p-methoxyphenylmethylidene group, 2-phenylethylidene group or (E)-3-phenyl-2-propenylidene group.

Furthermore, it is also possible to use such a compound where the diphenylmethyl group in the above-mentioned N-ethylidene diphenylmethylamine has been replaced by p-methoxy-phenyl group and the ethylidene group thereof has been replaced by substituted with propylidene group, butylidene group, 2-methylpropylidene group, pentylidene group, 3-methylbutylidene group, neopentylidene group, hexylidene group, 4-methylpentylidene group, neohexylidene group, tridecylidene group, tetradecylidene group, cyclopentylmethylidene group, cyclohexylmethylidene group, phenylmethylidene group, p-chlorophenylmethylidene group, p-fluorophenylmethylidene group, p-methoxyphenylmethylidene group, 2-phenylethylidene group or (E)-3-phenyl-2-propenylidene group.

Among these imines, N-ethylidene diphenylmethylamine, N-propylidene diphenylmethylamine, N-butylidene diphenylmethylamine and N-2-methylpropylidene diphenylmethylamine are most preferably used.

The phosphonic acid ester of the formula (III) used as a reactant in the process of the first aspect of this invention is the compound hitherto known and may be obtained by the method hitherto known.

Where $R^3$ in the phosphonic acid ester of the formula (III) is the alkyl group, such alkyl group includes those having 1 to 5 carbon atoms and may be of a straight or branched chain. An example of such alkyl group includes, particularly methyl group, ethyl group, n-propyl group, isopropyl group, n-butyl group, isobutyl group, sec-butyl group, tert-butyl group, n-pentyl group, isopentyl group, neopentyl group and the like. Among them, methyl group is most preferable.

Where $R^3$ in the formula (III) is the cycloalkyl group, an example of such cycloalkyl group includes particularly cyclopentyl group, cyclohexyl group and the like.

Where $R^3$ in the formula (III) is the aryl group, an example of such aryl group includes particularly phenyl group, p-tolyl group, p-chlorophenyl group and the like.

Where $R^3$ in the formula (III) is the aryl group-containing hydrocarbon radical, an example of such aryl group-containing hydrocarbon radical includes arylalkyl group such as benzyl group and phenethyl group; and aryl-vinyl group such as (E)-styryl group and p-methylphenylvinyl group ($CH_3$—$C_6H_4$—$CH$=$CH$—), similarly to those described for $R^2$.

Particular example of such phosphonic acid ester of the formula (III) can be dimethyl phosphite, diethyl phosphite, di-n-propyl phosphite, di-n-butyl phosphite, di-n-pentyl phosphite, diphenyl phosphite, dibenzyl phosphite, di-p-tolyl phosphite, di-p-chlorophenyl phosphite, dicyclohexyl phosphite, diallyl phosphite and the like.

Among these phosphonic acid esters, dimethyl phosphite is most preferably used.

The route of the reaction steps contained in the process of the first aspect of this invention can be depicted schematically by the following reaction equations:

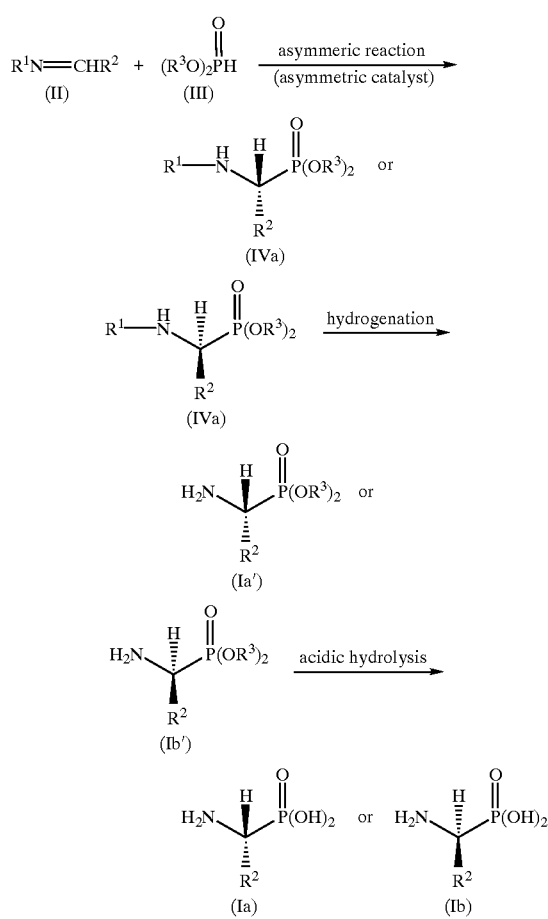

In the first step of the process of the first aspect of this invention, the imine of the formula (II) is asymmetrically reacted with the phosphonic acid ester of the formula (III) in the presence of such catalyst for asymmetric synthesis which consists of the above-mentioned complex, so that the compound of the formula (IVa) and/or the formula (IVb) is produced.

In such asymmetric reaction as above, the imine of the formula (II), the phosphonic acid ester of the formula (III) and the catalyst (A) for the asymmetric synthesis are preferably used in such proportions of them that the molar ratio of the imine:the phosphonic acid ester:the asymmetric catalyst is in the range of 1:1:0.01~1:5:1, preferably in the range of 1:1:0.01~1:5:0.2.

It is desirable that such asymmetric reaction is carried out usually at a temperature of −80 to 80° C., preferably 20 to 50° C. and usually for 0.1 to 100 hours, preferably 60 to 80 hours.

Further, a solvent may usually used be in the reaction, and example of such available solvent as the reaction medium includes concretely, tetrahydrofuran (THF), toluene, ethyl ether, dioxane, dimethyl sufoxide (DMSO), dimethyl formamide (DMF), hexamethylphosphoryl amide (HMPA) and the like. THF, toluene and ether are most preferably used.

Furthermore, in this asymmetric reaction, these solvents may be used alone or as a mixed solvent in which two or more solvents are mixed. An example of the mixed solvent includes, particularly a toluene-THF mixed solvent, a THF-dioxane mixed solvent, and the like. The toluene-THF mixed solvent is most preferable. Particularly, it is preferable to use the toluene-THF mixed solvent in which one volume of THF is mixed with 1 to 10 volumes, preferably 6 to 8 volumes of toluene.

Said asymmetric reaction can usually be stopped by adding to the resulting reaction solution water having a volume of 1 to 10 times larger than the volume of the reaction solution.

Subsequently, the resulting reaction solution containing the compound of the formula (IVa) or (IVb) is usually washed with an aqueous solution of sodium chloride and then separated into the aqueous layer and the organic layer. The organic layer thus obtained is distilled to evaporate off the solvent, thereby giving a crude product of the compound (IVa) or (IVb). The crude product thus obtained may be purified, for example, by silica gel column chromatography to give the compound of the formula (IVa) or (IVb).

A particular example of the compound of the formula (IVa) or (IVb) is (R)- or (S)-1-diphenylmethylaminoethylphosphonic acid dimethyl ester.

In addition, further examples of the compound (IVa) or (IVb) include such a compound where the dimethyl group of the said 1-diphenylmethylaminoethylphosphonic acid dimethyl ester is replaced by diethyl group, di-n-propyl group, di-isopropyl group, di-n-butyl group, di-isobutyl group, di-sec-butyl group, di-tert-butyl group, di-n-pentyl group, di-isopentyl group, di-neopentyl group, di-cyclopentyl group, di-cyclohexyl group, diphenyl group, dibenzyl group, di-p-tolyl group or di-p-chlorophenyl group. Furthermore, another example of the compound (IVa) or (IVb) includes such compound where the di-phenylmethyl group of the said 1-diphenylmethylaminoethylphosphonic acid dimethyl ester is replaced by p-methoxyphenyl group and the ethyl ester group thereof is replaced by propyl group, butyl group, 2-methylpropyl group, pentyl group, 3-methylbutyl group, neopentyl group, hexyl group, 4-methyl-pentyl group, neohexyl group, tridecyl group, tetradecyl group, cyclopentylmethyl group, cyclohexylmethyl group, phenylmethyl group, p-chlorophenylmethyl group, p-fluorophenymethyl group, p-methoxyphenylmethyl group, 2-phenyl-ethyl group or (E)-3-phenyl-2-propenyl group.

In the second step of the process according to the first aspect of this invention, the compound of the formula (IVa) or (IVb) is reduced with hydrogen to effect the deprotecting reaction of the protected amino group, thereby giving the compound of the formula (Ia') or (Ib'). Subsequently, in the third step of the process, an acid is admixed with the compound of the formula (Ia') or (Ib') and the hydrolytic reaction of the latter compound is effected to eliminate the ester-forming group $R^3$ therefrom.

Desirably, the deprotecting reaction of the protected amino group in the second step of the process is effected by the de-protection method according to a catalytic hydrogenation in such a way that palladium hydroxide on carbon, or palladium black is used as the catalyst usually in an amount of 0.1 to 10 times higher than, preferably 0.1 to 1 times higher than the amount of the compound of the formula (IVa) or (IVb) on the weight basis. In this catalytic hydrogenation, a solvent can be used as the reaction medium. An example of such solvent includes particularly acetic acid, methanol, ethanol and the like. Methanol is most preferably used. Desirably, the reaction temperature is usually 20 to 100° C., preferably 20 to 50° C. Desirably, the reaction time is usually 1 to 50 hours, preferably 3 to 10 hours. After the completion of the reaction, the resulting reaction solution is usually filtered to remove the catalyst made of palladium hydroxide on carbon or palladium black and then distilled to evaporate off the solvent therefrom. The residue so obtained is dissolved into water and washed with hexane, and the resulting aqueous layer is evaporated under a reduced pressure to give the compound of the formula (Ia') or (Ib').

Furthermore, an acid is used for the hydrolytic reaction in the third step of the process, and the acid may be used in an amount of 5 to 100 mols, preferably 5 to 10 mols per 1 mol of the compound of the formula (Ia') or (Ib'). An example of such acid includes particularly, concentrated hydrochloric acid having a concentration of 35%, or concentrated sulfuric acid, or acetic acid having a concentration of 100%, and the like. The concentrated hydrochloric acid or acetic acid is most preferably used.

The hydrolytic reaction can be carried out in the absence of any solvent (namely, without solvent) or in the solvent. An example of the solvent includes particularly methanol, chloroform, acetic acid, acetone and the like. Methanol or acetic acid is most preferably used. When the hydrolytic reaction is carried out in the absence of solvent, it is preferable to effect the reaction usually at 20 to 100° C., preferably at 80 to 100° C. When the reaction is carried out in the solvent, the reaction may desirably be effected usually at 20 to 100° C., preferably at a refluxing temperature of the solvent. When the reaction is effected under the condition of the absence of the solvent, the reaction time is desirably 1 to 10 hours, preferably 8 to 10 hours. When using the solvent, the reaction time is desirably 1 to 50 hours, preferably 10 to 20 hours. After the completion of the reaction, the resulting reaction solution may usually be distilled to evaporate off the solvent under a reduced pressure, thereby giving the compound of the formula (Ia) or (Ib).

Furthermore, the compound of the formula (IVa) or (IVb) may directly be contacted with an acid to effect the reactions for deprotecting the protected amino group and for hydrolyzing the group $OR^3$, so that the compound of the formula (Ia) or (Ib) is produced. The reaction conditions available here are the same as those for the hydrolytic reaction in the aforesaid third step of the process, except that the compound of the formula (Ia') or (Ib') is replaced by the compound of the formula (IVa) or (IVb).

An example of the thus obtained compound of the formula (Ia) or (Ib) is (R)- or (S)-1-aminoethylphosphonic acid.

In addition, another examples of the compound of the formula (Ia) or (Ib) include such a compound where the ethyl group in the above-mentioned (R)- or (S)-1-aminoethylphosphonic acid is replaced by propyl group, butyl group, 2-methylpropyl group, pentyl group, 3-methylbutyl group, neopentyl group, hexyl group, 4-methylpentyl group, neohexyl group, tridecyl group, tetradecyl group, cyclopentylmethyl group, cyclohexylmethyl group, phenylmethyl group, p-chlorophenylmethyl group, p-fluorophenylmethyl group, p-methoxyphenylmethyl group, 2-phenylethyl group or (E)-3-phenyl-2-propenyl group.

Furthermore, when the process of the first aspect of this invention is carried out in the presence of the rare earth element-alkali metal-binaphthol complex as the asymmetric catalyst, of which the binaphthol component is (R)-(+)-1,1'-bi-2-naphthol, the compound of the formula (Ia) obtained as the final target product is the (R)-enantiomer which is produced preferentially and constitutes a major product, and which is in admixture with a small amount of the compound of the formula (Ib), namely the (S)-enantiomer produced as a minor product. Whereas, when the process of the first aspect invention is carried out in the presence of the complex containing (S)-(−)-1,1'-bi-2-naphthol as the binaphthol component, the compound of the formula (Ib) which is preferentially produced is the (S)-enantiomer which constitutes a major product, and which is in admixture with a small amount of the compound of the formula (Ia), namely the (R)-enantiomer produced as a minor product. The admixture of the compound of the formula (Ia) with the compound of the formula (Ib) may be subjected to a chromatography or high performance liquid chromatography (HPLC) with a suitable developing solvent so that the compound of the formula (Ia) may be isolated from that of the formula (Ib).

Further, according to this invention, there is provided a method for the preparation of such a catalyst for use in the asymmetric synthesis, which is used in the process of the first aspect of this invention.

According to the second aspect of the present invention, therefore there is provided a method for the preparation of an asymmetric catalyst which consists of a complex of a rare earth element with an alkali metal and (R)-(+)-1,1'-bi-2-naphthol or (S)-(−)-1,1'-bi-2-naphthol, and which is for use in the asymmetric synthesis of an (R)- or (S)-1-aminophosphonic acid ester derivative by an asymmetric condensation reaction of an imine with a phosphonic acid ester, characterized in that said process comprises:

reacting in an anhydrous organic solvent or aqueous organic solvent (R)-2,2'-dihydroxy-1,1'-binaphthyl, namely (R)-(+)-1,1'-bi-2-naphthol represented by the formula ($V_R$):

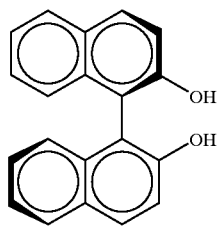

($V_R$)

or (S)-2,2'-dihydroxy-1,1'-binaphthyl, namely (S)-(−)-1,1'-bi-2-naphthol represented by the formula ($V_S$):

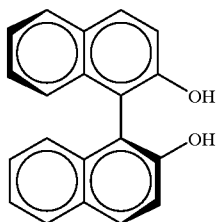

(V<sub>S</sub>)

with a rare earth element alkoxide represented by the general formula (VI):

$$Ln(OR)_3 \qquad (VI)$$

wherein Ln stands for a rare earth element and R stands for an alkyl group; and also with an alkali metal compound selected from a group consisting of:

an alkyl lithium represented by the general formula (VII):

$$LiR \qquad (VII)$$

wherein R stands for an alkyl group, and trimethylsilyl potassium amide represented by the general formula (VIII):

$$[(CH_3)_3Si]_2NK \qquad (VIII)$$

and an alkali metal alkoxide represented by the general formula (IX):

$$Z(OR) \qquad (IX)$$

wherein Z stands for an alkali metal and R stands for an alkyl group, in such proportions of these reactant compounds that the molar ratio between the compound of the formula ($V_R$) or ($V_S$), the rare earth element alkoxide of the formula (VI) and the alkali metal compound of the formula (VII), (VIII) or (IX) is in a range of 1~10:1:1~10, particularly in a range of 1~3:1:1~3, with the reaction being effected at a temperature of 0 to 50° C. but at a temperature of not higher than the boiling point of the solvent used, for 0.1 to 100 hours under an atmosphere of an inactive gas, thereby to produce said complex, and then collecting the complex from the resulting reaction solution as the catalyst for the asymmetric synthesis.

Both of the (R)-2,2'-dihydroxy-1,1'-binaphthyl, namely (R)-(+)-1,1'-bi-2-naphthol of the formula ($V_R$) and (S)-2,2'-dihydroxy-1,1'-binaphthyl, namely (S)-(−)-1,1'-bi-2-naphthol, which are used as the starting material in the method for the preparation of the asymmetric catalyst according to the second aspect of this invention, are known substances and may be prepared by the process hitherto known (refer to "Journal of Organic Chemistry", p.7317, 1993).

The rare earth element alkoxide of the formula (VI) used as the second starting material is also a known substance and may be prepared by known process. The rare earth element here present in said alkoxide can be the same as that used in the process of the first aspect invention, and thus may be scandium, yttrium, lanthanum, cerium, praseodymium, neodymium, promethium, samarium, europium, gadolinium, terbium, dysprosium, holmium, erbium, thulium, ytterbium or lutetium. A preferred example of the rare earth element alkoxide of the formula (VI) includes lanthanum tri-isopropoxide, lanthanum tri-t-butoxide, gadolinium tri-isopropoxide or praseodymium tri-isopropoxide.

The group R in the alkyl lithium compound of the formula (VII) represents alkyl group. An example of the alkyl group includes particularly, methyl group, n-butyl group, t-butyl group and the like. n-Butyl group is most preferable. An example of the compound of the formula (VII) includes especially $CH_3Li$, $CH_3(CH_2)_3Li$, $(CH_3)_3CLi$ and the like. n-Butyl lithium $CH_3(CH_2)_3Li$ is most preferably used.

Trimethylsilyl potassium amide of the formula (III) is a known substance.

In addition, the alkali metal alkoxide of the formula (IX) is also a known compound and can be prepared by the known process ["Journal of American Chemical Society" (JACS), p.4364, 1956].

In the alkali metal alkoxide of the formula (IX), an example of the alkali metal represented by Z includes Li, Na, K, Rb and Cs. Na or K is most preferably used. An example of the alkali metal alkoxide of the formula (IX) includes particularly $LiOC(CH_3)_3$, $NaOC(CH_3)_3$, $KOC(CH_3)_3$, $RbOC(CH_3)_3$, $CsOC(CH_3)_3$, $LiOCH(CH_3)_2$, $NaOCH(CH_3)_2$, $KOCH(CH_3)_2$, $RbOCH(CH_3)_2$, $CsOCH(CH_3)_2$ and the like. $LiOC(CH_3)_3$, $NaOC(CH_3)_3$, $KOC(CH_3)_3$, $RbOC(CH_3)_3$ or $CsOC(CH_3)_3$ is most preferably used.

In the method of the second aspect of this invention, it is desirable that the 1,1'-bi-2-naphthol of the formula ($V_R$) or ($V_S$), the rare earth element alkoxide of the formula (VI) and the alkali metal compound of the formula (VII), (VIII) or (IX) are used and reacted each other in such proportions that they are used generally in a range of the molar ratio of usually 1~10:1:1~10 and preferably in a molar ratio range of 1~3:1:1~3. In addition, it is desirable that the reaction for formation of the complex is effected at a temperature of 0 to 50° C. and preferably at a temperature of 0 to 20° C. and usually for a time of 0.1 to 100 hours and preferably for a time of 0.1 to 24 hours.

In the method of the second aspect of this invention, the above reaction may be effected in a non-aqueous or aqueous organic solvent. An example of the organic solvent includes, particularly, tetrahydrofuran (hereinafter referred to as "THF"), ethyl ether and the like. THF is most preferably used.

An example of the aqueous organic solvent includes aqueous THF, an aqueous ether, aqueous dioxane, aqueous diethyl ether and the like. Aqueous THF or aqueous ethyl ether is most preferably used.

Where the aqueous organic solvent is used as the reaction medium in the method of the second aspect invention, it is preferable that water is present in an amount of usually 0.1 to 10 mols, preferably 0.1 to 1 mol per one mol of the rare earth element compound of the formula (VI).

In the method of the second aspect of this invention, the reaction between the bi-naphthol compound of the formula ($V_R$) or ($V_S$), the rare earth element alkoxide of the formula (VI) and the alkali metal compound of the formula (VII), (VIII) or (IX) may be effected at a temperature of 0 to 50° C. under the atmosphere of an inactive gas, preferably nitrogen or argon gas. However, the reaction is preferable to be effected at a temperature as low as possible.

By this reaction, one atom of the rare earth element, three atoms of the alkali metal and three molecules of the binaphthol compound used will combine with each other to form the intended complex compound. But, it is very much probable that this complex compound has the structure of the formula (a) or (b), as described hereinbefore in respect of the complex which constitutes the asymmetric catalyst to be used in the process of the first aspect of this invention.

In the method of the second aspect of this invention, the complex compound which is formed by the reaction of the bi-naphthol compound of the formula ($V_R$) or ($V_S$) with the rare earth element alkoxide of the formula (VI) and the alkali metal compound having any one of the formula (VII) to (IX) and which is namely the substance abbreviated as the "rare earth element alkoxide-alkali metal-binaphthol complex", is then collected from the resulting reaction solution after the complex-forming reaction. The collection of the complex may preferably be effected by evaporating the solvent together with the by-products off from said reaction solution at a temperature of not higher than 30° C., preferably of 10 to 20° C. under a reduced pressure, and then adding a fresh organic solvent, for example, an organic solvent destined to be used in the first step of the process of the first aspect invention, such as THF, toluene, a THF-toluene mixed solvent or a THF-dioxane mixed solvent, to the resulting residue or the resulting concentrated solution, and subsequently dissolving the complex compound in said fresh solvent. The complex compound which has been thus transferred into the fresh organic solvent can retain its catalytic activity for a long time.

An example of the rare earth element-containing complex obtained as the reaction product according to the method of the second aspect of this invention includes the following complexes:

such a complex which is assumed to have such structure that three (R)-(+)-1,1'-bi-2-naphthol molecules have combined with one lanthanum atom and further three lithium atoms have complexed with totally six oxygen atoms of the bi-naphthol moieties to form said complex (hereinafter, this particular complex is abbreviated as "(R)-La-Li-B-complex"), such a complex which is assumed to have such structure that three (R)-(+)-1,1'-bi-2-naphthol molecules have combined with one lanthanum atom and further three potassium atoms have complexed with totally six oxygen atoms of the bi-naphthol moieties to form said complex (hereinafter, this particular complex is abbreviated as "(R)-La-K-B-complex");

such a complex which is assumed to have such structure that three (R)-(+)-1,1'-bi-2-naphthol molecules have combined with one lanthanum atom and further three sodium atoms have complexed with totally six oxygen atoms of the binaphthol moieties to form said complex (hereinafter, this particular complex is abbreviated as "(R)-La-Na-B-complex");

such a complex which is assumed to have such structure that three (R)-(+)-1,1'-bi-2-naphthol molecules have combined with one lanthanum atom and further three rubidium or cesium atoms have complexed with totally six oxygen atoms of the binaphthol moieties to form said complex (hereinafter, this particular complex is abbreviated as "(R)-La-Rb- or Cs-B-complex"); and such a complex which is assumed to have such structure that three (S)-(−)-1,1'-bi-2-naphthol molecules have combined with one lanthanum atom and further three lithium atoms have complexed with totally six oxygen atoms of the bi-naphthol moieties to form said complex (hereinafter, this particular complex is abbreviated as "(S)-La-Li-B-complex"): as well as another analogues thereof. The lanthanum atom which is present in the chemical structures of the different complexes as exemplified in the above, for example, the "(R)-La-Li-B-complex", "(R)-La-K-B-complex" and "(R)-La-Na-B-complex", is exchangeable by Sc, Y, Ce, Pr, Nd, Pm, Sm, Eu, Gd, Tb, Dy, Ho, Er, Tm, Yb or Lu atom. Besides, the moiety of (R)-(+)-1,1'-2-naphthol molecule is exchangeable by (S)-(−)-1,1'-2-naphthol. Further, the Li, K or Na atom respectively is exchangeable by rubidium (Rb) or cesium (Cs).

When the different complexes as exemplified in the above, which are the catalysts prepared by the method of the second aspect invention, are used as the asymmetric catalyst in the asymmetric reaction according to the present invention, it appears that the "(R)- or (S)-La-K-B-complex" has a highest catalytic activity and the "(R)- or (S)-La-Na-B-complex" has a secondly high catalytic activity. As compared with these two complexes, the "(R)- or (S)-La-Li-B-complex", "(R)- or (S)-La-Rb-B-complex" and "(R)- or (S)-La-Cs-B-complex" have lower catalytic activities.

Furthermore, it has now been found that some members of the N-protected-1-aminophosphonic acid ester derivatives of the formula (IVa) or (IVb), which are obtained as an intermediate in the first step of the process of the first aspect invention, are novel compounds and are useful for the preparation of the compound of the formula (Ia) or (Ib) in accordance with the process of the first aspect invention.

According to a third aspect of this invention, therefore, there is provided, as a novel substance, a new (R)- or (S)-N-protected-1-aminophosphonic acid alkyl ester represented by the general formula (IVa-1) or (IVb-1):

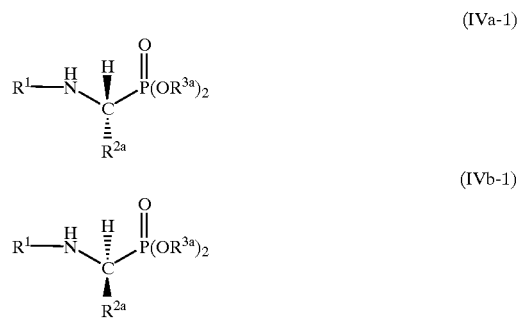

wherein $R^1$ stands for diphenylmethyl group or an alkoxyphenyl group, $R^{2a}$ stands for an alkyl group, a cycloalkyl group or an aryl group, or $R^{2a}$ stands for an aryl group optionally substituted with a halogen atom or an alkoxy group, and $R^{3a}$ stands an alkyl group.

A preferable example of the 1-aminophosphonic acid ester derivative of the formula (IVa-1) or (IVb-1) according to the third aspect of this invention includes the following compounds (1) to (17):

(1) an optically active (R)- or (S)-1-diphenylmethylamino-2-methylpropylphosphonic acid dimethyl ester of the formula (IVa-1) or (IVb-1), wherein $R^1$ is diphenylmethyl group, $R^{2a}$ is isopropyl group and $R^{3a}$ is methyl group;

(2) an optically active (R)- or (S)-1-diphenylmethylamino-hexylphophonic acid dimethyl ester of the formula (IVa-1) or (IVb-1), wherein $R^1$ is diphenylmethyl group, $R^{2a}$ is n-pentyl group and $R^{3a}$ is methyl group;

(3) an optically active (R)- or (S)-1-diphenylmethylamino-propylphosphonic acid dimethyl ester of the formula (IVa-1) or (IVb-1), wherein $R^1$ is diphenylmethyl group, $R^{2a}$ is ethyl group and $R^{3a}$ is methyl group;

(4) an optically active (R)- or (S)-(E)-1-diphenylmethylamino-3-phenyl-2-propenylphosphonic acid dimethyl ester of the formula (IVa-1) or (IVb-1), wherein $R^1$ is diphenylmethyl group, $R^{2a}$ is (E)-styryl group and $R^{3a}$ is methyl group;

(5) an optically active (R)- or (S)-1-p-methoxyphenylamino-cyclohexylmethylphosphonic acid dimethyl ester of the formula (IVa-1) or (IVb-1), wherein $R^1$ is p-methoxyphenyl group, $R^{2a}$ is cyclohexyl group and $R^{3a}$ is methyl group;

(6) an optically active (R)- or (S)-1-diphenylmethylamino-ethylphosphonic acid dimethyl ester of the formula (IVa-1) or (IVb-1), wherein R is diphenylmethyl group, $R^{2a}$ is methyl group and $R^{3a}$ is methyl group;

(7) an optically active (R)- or (S)-1-diphenylmethylamino-butylphosphonic acid dimethyl ester of the formula (IVa-1) or (IVb-1), wherein $R^1$ is diphenylmethyl group, $R^{2a}$ is n-propyl group and $R^{3a}$ is methyl group;

(8) an optically active (R)- or (S)-1-diphenylmethylamino-pentylphosphonic acid dimethyl ester of the formula (IVa-1) or (IVb-1), wherein $R^1$ is diphenylmethyl group, $R^{2a}$ is n-butyl group and $R^{3a}$ is methyl group;

(9) an optically active (R)- or (S)-1-diphenylmethylamino-tridecylphosphonic acid dimethyl ester of the formula (IVa-1) or (IVb-1), wherein $R^1$ is diphenylmethyl group, $R^{2a}$ is dodecyl group and $R^{3a}$ is methyl group;

(10) an optically active (R)- or (S)-1-diphenylmethylamino-3-methylbutylphosphonic acid dimethyl ester of the formula (IVa-1) or (IVb-1), wherein $R^1$ is diphenylmethyl group, $R^{2a}$ is isobutyl group and $R^{3a}$ is methyl group;

(11) an optically active (R)- or (S)-1-diphenylmethylamino-phenylmethylphosphonic acid dimethyl ester of the formula (IVa-1) or (IVb-1), wherein $R^1$ is diphenylmethyl group, $R^{2a}$ is phenyl group and $R^{3a}$ is methyl group;

(12) an optically active (R)- or (S)-1-diphenylmethylamino-p-chlorophenylmethylphosphonic acid dimethyl ester of the formula (IVa-1) or (IVb-1), wherein $R^1$ is diphenylmethyl group, $R^{2a}$ is p-methoxyphenyl group and $R^{3a}$ is methyl group;

(13) an optically active (R)- or (S)-1-diphenylmethylamino-p-fluorophenylmethylphosphonic acid dimethyl ester of the formula (IVa-1) or (IV-1), wherein $R^1$ is diphenylmethyl group, $R^{2a}$ is p-fluorophenyl group and $R^{3a}$ is methyl group;

(14) an optically active (R)- or (S)-1-diphenylmethylamino-p-methoxyphenylmethylphosphonic acid dimethyl ester of the formula (IVa-1) or (IVb-1), wherein $R^1$ is diphenylmethyl group, $R^{2a}$ is p-methoxyphenyl group and $R^{3a}$ is methyl group;

(15) an optically active (R)- or (S)-1-diphenylmethylamino-2-phenylethylphosphonic acid dimethyl ester of the formula (IVa-1) or (IVb-1), wherein $R^1$ is diphenylmethyl group, $R^{2a}$ is benzyl group and $R^{3a}$ is methyl group; and

(16) an optically active (R)- or (S)-1-p-methoxyphenylamino-1-cyclohexylmethylphosphonic acid dimethyl ester of the formula (IVa-1) or (IVb-1), wherein $R^1$ is p-methoxyphenyl group, $R^{2a}$ is cyclohexyl group and $R^{3a}$ is methyl group.

Furthermore, the optical purity of the optically active compound of the formula (Ia) or (Ib), which is obtained by the process of the first aspect invention, can be determined by a conventional method of measurement which comprises subjecting said optically active compound to a chromatography, and calculating the ratio between the area under the absorption peak of the (R)-enantiomer and the area under the absorption peak of (S)-enantiomer on the resulting chromatogram and further evaluating percentages of enantiometric excess (ee.) from the calculated ratio of the areas under peak.

Also, in Examples of working the process of the first aspect invention, the percentage of enantiometric excess (ee.) of the compound of the formula (Ia) or (Ib) as obtained was determined by the conventional method. Namely, the finally target product as obtained in Examples of working the process of the first aspect invention was subjected to a high performance liquid chromatography (HPLC) to draw on the resulting chromatogram a curve of depicting changes in the absorption peak of the (R)-enantiomer and in the absorption peak of the (S)-enantiomer against the retention time (minutes) lapsed. An example of the chromatogram thus obtained is shown in FIG. 1 of the attached drawing.

The optical purity of the final end product can be evaluated by calculating the area under the absorption peak of (R)-enantiomer (area value:A) and the area under the absorption peak of (S)-enantiomer (area value:B) from said chromatogram obtained as above, and calculating the ratio of the area to area(value A/B=γ) from the values of A and B, and calculating the absolute value of the remainder by subtracting the value A from the value B, as well as the sum of the value B plus the value A, and further calculating the percentages of enantiometric excess according to the calculation equation below:

Percentages of enantiometric excess (ee.)=

$$\text{Percentages of enantiometric excess (ee.)} = \frac{|B-A|}{(B+A)} \times 1 = \frac{|1-\gamma|}{(1+\gamma)} \times 1$$

BEST MODE FOR WORKING THE INVENTION

Figure 1:
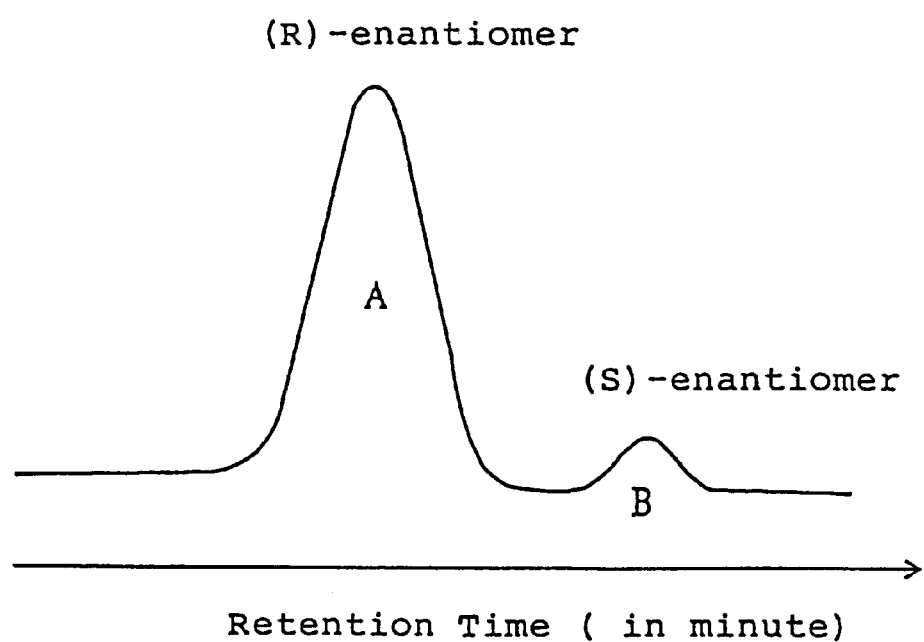
FIG. 1 of the attached drawing shows a chromatogram drawn in order to evaluate the percentage of enantiomer excess (ee.) of a particular example of (R)-1-aminophosphonic acid derivative as obtained in Example of working the process of the first aspect invention.

The inventions will be now further illustrated with reference to the following Examples but are not limited thereto.

Firstly, Examples 1 to 4 given below illustrate the preparation of the rare earth element-alkali metal-binaphthol complex useful as the asymmetric catalyst, according to the method of the second aspect of this invention.

EXAMPLE 1

Preparation of (R)-La-K-binaphthol complex

To 4.29 g (5×3 mmol) of (R)-(+)-1,1'-bi-2-naphthol were added 25 ml of a solution in THF of 0.2M lanthanum tri-isopropoxide La[OCH(CH$_3$)$_2$]$_3$ (containing a total amount of lanthanum tri-isopropoxide of 5 mmol as calculated), 30 ml of a solution in toluene of 0.5M bis(trimethylsilyl) potassium amide (containing a total amount of bis(trimethylsilyl) potassium amide of 5×3 mmol as calculated), 90 mg of water (5 mmol) and 45 ml of THF under the atmosphere of nitrogen. The resulting reaction mixture was stirred at 20° C. (a room temperature) for one hour to effect the reaction. By this reaction, there was produced such a complex in which three molecules of (R)-(+)-1,1'-bi-2-naphthol have combined with one atom of La and three atoms of potassium have combined with the naphthol moieties via the complexing bond [this complex is abbreviated as (R)-La-K-binaphthol complex or (R)-La-K-B-complex]. This complex was contained in the resulting reaction solution at a concentration of about 0.05 mol/liter. The yield of this complex was 100%.

From the reaction solution containing the (R)-La-K-B-complex so produced were evaporated off THF, toluene and water as the solvents, as well as the by-products at a temperature of 15 to 20° C. under a reduced pressure of 5 mmHg. Thus, the complex was obtained as the residue. Then, to the residue was added 100 ml of a THF-toluene (1:7 by volume) mixed solvent to dissolve the complex therein. A solution containing the complex at a concentration of about 0.05 mol/liter was afforded.

The resulting solution of the complex, even after its storage for 2 weeks, was utilizable as a solution containing the asymmetric catalyst which was useful for the asymmetric reaction of an imine with an N-protected-1-aminophosphonic acid ester according to the process of the first aspect invention.

The (R)-La-K-B-complex as obtained in this Example is the complex having the a presumed chemical structure of formula(a-1):

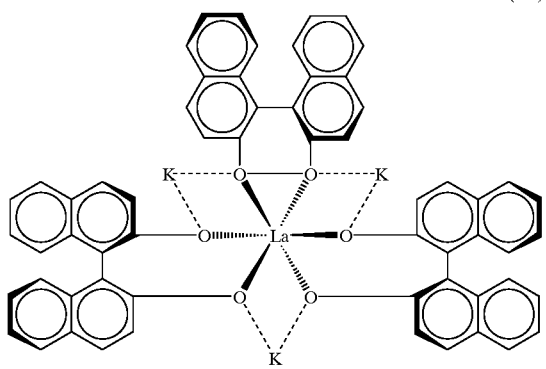

(a-1)

where La stands for a lanthanum atom and K stands for a potassium atom.

EXAMPLE 2

Preparation of (S)-La-K-binaphthol complex

To 4.29 g (5×3 mmol) of (S)-(−)-1,1'-bi-2-naphthol, were added 25 ml of a solution of 0.2M lanthanum tri-isopropoxide in THF, 30 ml of a solution of 0.5M bis(trimethylsilyl) potassium amide in toluene (5×3 mmol), 90 mg of water (5 mmol) and 45 ml of THF under the atmosphere of nitrogen. The resulting reaction mixture was stirred at 20° C. (a room temperature) for one hour to effect the reaction. By this reaction, there was produced such a complex in which three molecules of (S)-(−)-1,1'-bi-2-naphthol have combined with one atom of La and three atoms of K have combined with the naphthol moieties by the complexing bond [this complex is abbreviated as (S)-La-K-binaphthol complex or (S)-La-K-B-complex]. This complex was contained in the resulting reaction solution at a concentration of about 0.05 mol/liter. Its yield was 100%.

From the resulting reaction solution containing the (S)-La-K-B-complex, the solvents and others were distilled off at a temperature of 15 to 20° C. under a reduced pressure of 5 mmHg. The complex was obtained as the residue. Then, 100 ml of a THF-toluene (1:7 by volume) mixed solvent was added to the residue to dissolve the complex therein. Thus, a catalyst solution containing the complex at a concentration of about 0.05 mol/liter was afforded.

The (S)-La-K-B-complex as obtained in this Example is the complex having a presumed chemical structure of formula(b-1):

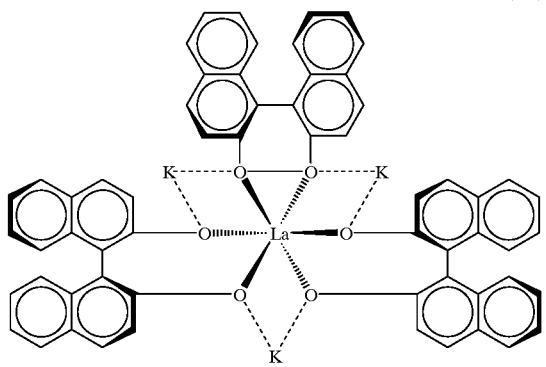

(b-1)

where La stands for a lanthanum atom and K stands for a potassium atom.

EXAMPLE 3

Preparation of (R)-Gd-K-binaphthol complex

The procedure of Example 1 was repeated in the same way as in Example 1, except that 25 ml of a solution of gadolinium tri-isopropoxide Gd[OCH(CH$_3$)$_2$ ]$_3$ in THF (containing a total amount of lanthanum tri-isopropoxide of 5 mmol as calculated) was used in place of 25 ml of the solution of 0.2 M lanthanum tri-isopropoxide in THF which was used in the reaction of Example 1.

There was obtained a reaction solution containing as the reaction product such a complex in which three (R)-(+)-1,1'-bi-2-naphthol molecules have combined with one atom of Gd and three atoms of K have combined with the naphthol moieties by the complexing bond [this complex is abbreviated as (R)-Gd-K-binaphthol complex or (R)-Gd-K-B-complex]. The reaction solution contained the complex at a concentration of about 0.05 mol/liter (yield of 100%).

From the reaction solution, the solvents were removed by distillation under a reduced pressure. Then, 100 ml of a THF-toluene (1:7 by volume) mixed solvent was added to the resulting residue to dissolve the complex therein. A catalyst solution containing (R)-Gd-K-B-complex at a concentration of about 0.05 mol/liter was thus afforded.

EXAMPLE 4

Preparation of (R)-Pr-K-binaphthol complex

The procedure of Example 1 was repeated in the same way as in Example 1, except that 25 ml of a solution of praseodymium tri-isopropoxide Pr[OCH(CH$_3$)$_2$]$_3$ in THF (containing a total amount of lanthanum tri-isopropoxide of 5 mmol as calculated) was used in place of 25 ml of the solution of 0.2 M lanthanum tri-isopropoxide in THF which was used in the reaction of Example 1.

There was obtained a reaction solution containing as the reaction product such a complex in which three (R)-(+)-1,1'-bi-2-naphthol molecules have combined with one atom of Pr and three atoms of K have combined with the naphthol moieties by the complexing bond [this complex is abbreviated as (R)-Pr-K-binaphthol complex or (R)-Pr-K-B-complex]. The reaction solution contained the complex at a concentration of about 0.05 mol/liter (yield of 100%).

From the reaction solution, the solvents were distilled off under a reduced pressure. Then, 100 ml of a THF-toluene (1:7 by volume) mixed solvent was added to the resulting residue to dissolve the complex therein. A catalyst solution containing (R)-Pr-K-B-complex at a concentration of about 0.05 mol/liter was thus afforded.

Next, Examples 5 to 22 given below illustrate the preparation of (R)- or (S)-1-aminophosphonic acid derivatives according to the process of the first aspect of this invention.

EXAMPLE 5

Preparation of (R)-1-amino-2-methylpropylphosphonic acid [an example of the compound of formula (Ia)]

(1) Preparation of dimethyl (R)-1-diphenylamino-2-methylpropylphosphonate [an example of the compound of formula (IVa)] by the asymmetric reaction in the presence of the (R)-La-K-B-complex.

To a mixture of 0.30 g (1.25 mmol) of N-2-methylpropylidene diphenylmethyl amine [an example of the compound of formula (II)] with 0.21 g (1.25×1.5 mmol) of dimethyl phosphonate, namely dimethyl phosphite $[(CH_3O)_2P(O)H]$ [an example of the compound of formula (III)] was added 5 ml of a solution containing the (R)-La-K-B-complex of Example 1 at a concentration of 0.05 mol/liter in a mixed solvent of THF-toluene (1:7) [containing a total amount of (R)-La-K-B-complex of 1.25× 0.2 mmol which was corresponding to a proportion of 20 mol % per 1 mol of the amine compound]. The resulting mixture was well mixed.

The resulting reaction mixture was stirred at 20° C. for 56 hours to effect an asymmetric reaction, and thereafter 10 ml of water was added to the resultant reaction solution to stop the reaction.

Then, for the post-treatment, an aqueous solution of sodium chloride was added to wash the reaction solution. Thereafter the aqueous layer and the organic layer were separated from each other. The organic layer was distilled under reduced pressure to remove the solvents therefrom. A crude product of the target compound was obtained as the residue. The crude product was purified by a silica gel column chromatography [the silica gel column of 30 cm length×20 cm diameter; as developed with an ethyl acetate-hexane (1:1 by volume) mixed solvent]. In this way, 400 mg of dimethyl (R)-1-diphenylmethylamino-2-methylpropylphosphonate was obtained as the titled compound (yield of 92%). The (R)-enantiomer here obtained showed physical properties given below:

$[\alpha]_D$–59.8° (c=1.4, $CHCl_3$)

$^1$H-NMR($CDCl_3$) of dimethyl (R)-1-diphenyl-dimethylamino-2-methylpropylphosphonate showed the following peak values:

δ: 7.38–7.45(m, 4H), 7.17–7.34(m, 6H), 5.22(d, J=3.8 Hz, 1H), 3.77(d, J=10.2 Hz, 3H), 3.72(d, J=10.6 Hz, 3H), 2.78(br d, J=13.5 Hz, 1H), 2.08–2.13(m, 1H), 1.88(br s, 1H), 1.00–1.05(m, 6H).

In order to evaluate the optical purity of the (R)-enantiomer thus obtained, this compound was subjected to high performance liquid chromatography (HPLC) on the column of DAICEL CHIRALPAK AD supplied by Daicel Chemical Industry Co., Ltd. and with a mobile phase comprising an isopropyl alcohol-n-hexane (1:9) mixed solvent, to determine the chromatogram. Upon calculating the percentage of enantiometric excess (ee) of the (R)-enantiomer product from its chromatogram, it was found that the ee-value thereof was 97%.

(2) Preparation of dimethyl (R)-1-amino-2-methylpropylphosphonate [an example of the compound of the formula (Ia')] with elimination of the amino-protecting group by catalytic hydrogenation To 1.74 g (5 mmol) of dimethyl (R)-1-diphenylmethyl-amino-2-methylpropylphosphonate as obtained in the step (1) above were added 174 mg of palladium hydroxide carried on carbon and 10 ml of methanol, followed by well-mixing. Into the resulting mixture, hydrogen gas was blown at 20° C. for 4 hours under normal pressures while the mixture was stirred. In this way, hydrogenation reaction was effected to eliminate the diphenylmethyl group which was the amino-protecting group. The resulting reaction solution was filtered through a membrane filter, and the filtrate was distilled under a reduced pressure to remove the solvent therefrom.

To the residue, 10 ml of water was added, and the resulting solution was washed with 10 ml of hexane and then separated into two layers. The aqueous layer (an aqueous solution) so obtained was distilled under a reduced pressure to remove water. In this way, 906 mg of dimethyl (R)-1-amino-2-methylpropylphosphonate was obtained (yield 100%).

(3) Preparation of (R)-1-amino-2-methylpropylphosphonic acid [an example of the compound of formula (Ia)] with elimination of the ester-forming group by acidic hydrolysis.

To 906 mg (5 mmol) of dimethyl (R)-1-amino-2-methylpropylphosphonate obtained in the step (2) above, was added 20 ml of 35% hydrochloric acid. The resulting mixture was stirred at 100° C. for 8 hours. In this way, the acidic hydrolysis was effected. When the resulting reaction solution was distilled under a reduced pressure, to remove water, crude crystals were produced. The crude crystals were recrystallized from 10 ml of water to give 689 mg (yield 90%) of (R)-1-amino-2-methylpropylphosphonic acid [an example of the compound of formula (Ia)] as the final target product. This compound showed specific rotation: $[\alpha]_D$–2.4° (c=2.4, water). According to the literature, said compound shows a specific rotation of $[\alpha]_D$–2.1° (c=1.9, water).

The (R)-1-amino-2-methylpropylphosphonic acid so obtained in this Example was subjected to HPLC on the column of SUMI-CHIRAL OA-5000 supplied by Sumitomo Chemical Analytical Center, and the measurement of chromatogram was conducted using a mixture of a solution of 2 mM cupric(II) sulfate in water with $CH_3CN$ (9:1) as a mobile phase. When the percentage of enantiometric excess (ee) of the above (R)-enantiomer was calculated from its chromatogram, it was found that the ee value thereof was over 99%.

EXAMPLES 6 to 22

(1) The asymmetric reaction of the compound of the formula (II) with the compound of the formula (III) was conducted in the same manner as in Example 1 (1), except that either N-2-methylpropylidene diphenyl methyl amine as used in Example 5 (1), or a compound of the formula (II) shown in Table 1 was employed in the amount given in Table 1 and that dimethyl phosphonate [a compound of the formula (III)] was employed in the amount given in Table 1. This asymmetric reaction was conducted also in the presence of a catalyst for the asymmetric synthesis which were used in the amount given in Table 1 and which is any one of (R)-La-K-B-complex, (S)-La-K-B-complex, (R)-Gd-K-B-complex and (R)-Pr-K-B-complex prepared in Examples 1 to 4, while the reaction was effected under the conditions of the reaction temperature and the reaction time indicated in Table 1.

In this way, the various compounds of the formula (IVa) or (IVb) corresponding to the starting materials used were obtained as the asymmetric reaction product in the amounts and yields and at the percentages of enantiometric excess (ee) indicated in Table 1 (continued) below.

(2) The resultant compound of the formula (IVa) or (IVb) was used in the amount given in Table 1 (continued) and subjected to a hydrogenation reaction in the presence of palladium catalyst in the same manner as in Example 1 (2) so that the corresponding compound of the formula (Ia') or (Ib') was produced.

(3) The compound so obtained of the formula (Ia') or (Ib') was then hydrolyzed with 35% hydrochloric acid in the same manner as in Example 1 (3) so that the corresponding compound of the formula (Ia) or (Ib) was obtained in the amount and yield and at the percentage of enantiometric excess (ee) indicated in Table 1 (continued) below.

Furthermore, the steric configuration of the compound so obtained of the formula (Ia) or (Ib) is given in Table 1 (continued) by the symbol R or S so as to represent whether it was (R)-enantiomer or (S)-enantiomer.

The experimental features and reaction conditions which were used in Examples 6 to 23, including Example 5, as well as the results obtained are summarized in Table 1 and Table 1 (continued).

TABLE 1

| Ex. | Compound of formula (II) | | | Compound of formula (III) | | Complex as assymmetric catalyst (Amount, mol %) | Reaction Temperature (° C.) | Reaction Time (h) |
| --- | --- | --- | --- | --- | --- | --- | --- | --- |
| | $R^1$ | $R^2$ | Amount [g, (mmol)] | $R^3$ | Amount [g, (mmol)] | | | |
| 5 | (C$_6$H$_5$)$_2$CH– | (CH$_3$)$_2$CH | 0.30 (1.25) | CH$_3$ | 0.21 (1.875) | (R)—La—K—B(20) | 20 | 56 |
| 6 | (C$_6$H$_5$)$_2$CH– | (CH$_3$)$_2$CH | 0.30 (1.25) | CH$_3$ | 0.69 (6.25) | (R)—La—K—B(5) | 20 | 56 |
| 7 | (C$_6$H$_5$)$_2$CH– | n-C$_5$H$_{11}$ | 0.33 (1.25) | CH$_3$ | 0.69 (6.25) | (R)—La—K—B(20) | 20 | 87 |
| 8 | (C$_6$H$_5$)$_2$CH– | C$_2$H$_5$ | 0.28 (1.25) | CH$_3$ | 0.69 (6.25) | (R)—La—K—B(20) | 20 | 63 |
| 9 | (C$_6$H$_5$)$_2$CH– | (CH$_3$)$_2$CH | 0.30 (1.25) | CH$_3$ | 0.69 (6.25) | (S)—La—K—B(20) | 20 | 56 |
| 10 | (C$_6$H$_5$)$_2$CH– | C$_6$H$_5$–CH=CH | 0.37 (1.25) | CH$_3$ | 0.69 (6.25) | (R)—Gd—K—B(20) | 20 | 69 |
| 11 | (C$_6$H$_5$)$_2$CH– | C$_6$H$_5$–CH=CH | 0.37 (1.25) | CH$_3$ | 0.69 (6.25) | (R)—Gd—K—B(20) | 50 | 40 |
| 12 | CH$_3$O–C$_6$H$_4$– | C$_6$H$_{11}$ | 0.27 (1.25) | CH$_3$ | 0.69 (6.25) | (R)—Pr—K—B(20) | 20 | 68 |
| 13 | (C$_6$H$_5$)$_2$CH– | CH$_3$ | 0.26 (1.25) | CH$_3$ | 0.21 (1.875) | (R)—La—K—B(20) | 20 | 62 |

TABLE 1-continued

| Ex. | R³ | R⁴ | | | | | |
|---|---|---|---|---|---|---|---|
| 14 | (C₆H₅)₂CH- | n-C₃H₇ | 0.30 (1.25) | CH₃ | 0.21 (1.875) | (R)—La—K—B(20) | 20 | 62 |
| 15 | (C₆H₅)₂CH- | n-C₄H₉ | 0.31 (1.25) | CH₃ | 0.21 (1.875) | (R)—La—K—B(20) | 20 | 62 |
| 16 | (C₆H₅)₂CH- | n-C₁₂H₂₅ | 0.45 (1.25) | CH₃ | 0.21 (1.875) | (R)—La—K—B(20) | 20 | 62 |
| 17 | (C₆H₅)₂CH- | (CH₃)₂CHCH₂ | 0.31 (1.25) | CH₃ | 0.21 (1.875) | (R)—La—K—B(20) | 20 | 62 |
| 18 | (C₆H₅)₂CH- | C₆H₅ | 0.34 (1.25) | CH₃ | 0.21 (1.875) | (R)—La—K—B(20) | 20 | 62 |
| 19 | (C₆H₅)₂CH- | Cl-C₆H₄ | 0.38 (1.25) | CH₃ | 0.21 (1.875) | (R)—La—K—B(20) | 20 | 62 |
| 20 | (C₆H₅)₂CH- | F-C₆H₄ | 0.36 (1.25) | CH₃ | 0.21 (1.875) | (R)—La—K—B(20) | 20 | 62 |
| 21 | (C₆H₅)₂CH- | CH₃O-C₆H₄ | 0.38 (1.25) | CH₃ | 0.21 (1.875) | (R)—La—K—B(20) | 20 | 62 |
| 22 | (C₆H₅)₂CH- | C₆H₅CH₂ | 0.36 (1.25) | CH₃ | 0.21 1.875 | (R)—La—K—B(20) | 20 | 62 |

| | Intermediate of formula (IVa) or (IVb) | | | Product of formula (Ia) or (Ib) | | | | |
|---|---|---|---|---|---|---|---|---|
| Ex. | Amount obtained (mg) | Yield (%) | ee (%) | Amount used [g, (mmol)] | Amount obtained (mg) | Yield (%) | ee (%) | configuration |
| 5 | 400 | 92 | 97 | 1.74(5) | 689 | 90 | >99 | R |
| 6 | 356 | 82 | 92 | 1.74(5) | 704 | 92 | >99 | R |
| 7 | 408 | 87 | 85 | 1.88(5) | 815 | 90 | 95 | R |
| 8 | 367 | 88 | 94 | 1.67(5) | 632 | 91 | 97 | R |
| 9 | 369 | 85 | 96 | 1.74(5) | 689 | 90 | >99 | S |
| 10 | 244 | 48 | 69 | 2.04(5) | 959 | 90 | 94 | R |
| 11 | 438 | 86 | 86 | 2.04(5) | 981 | 92 | 95 | R |
| 12 | 307 | 75 | 66 | 1.64(5) | 869 | 90 | 96 | R |
| 13 | 319 | 80 | 82 | 1.60(5) | 576 | 92 | 97 | R |
| 14 | 391 | 90 | 92 | 1.74(5) | 712 | 93 | 95 | R |
| 15 | 384 | 85 | 90 | 1.81(5) | 785 | 94 | 96 | R |
| 16 | 355 | 60 | 70 | 2.37(5) | 1118 | 80 | 96 | R |
| 17 | 397 | 88 | 91 | 1.81(5) | 760 | 91 | 97 | R |
| 18 | 262 | 55 | 59 | 1.91(5) | 796 | 85 | 95 | R |
| 19 | 302 | 58 | 62 | 2.08(5) | 997 | 90 | 95 | R |

TABLE 1-continued

| | | | | | | | | |
|---|---|---|---|---|---|---|---|---|
| 20 | 300 | 60 | 66 | 2.00(5) | 913 | 89 | 95 | R |
| 21 | 319 | 62 | 68 | 2.06(5) | 923 | 85 | 95 | R |
| 22 | 346 | 70 | 70 | 1.98(5) | 805 | 80 | 95 | R |

Furthermore, the physical properties of dimethyl (R)-1-diphenylmethylamino-2-methylpropylphosphonate of formula (IVa) obtained as the intermediate and of (R)-1-amino-2-methyl-propylphosphonic acid of the formula (Ia) obtained as the final product in Example 6 were identical to those of the corresponding compounds obtained in Example 5, respectively.

The chemical name and physical properties of the compounds of the formula (IVa) or (IVb) which were obtained as the intermediate in each asymmetric reaction step of Examples 7 to 23 are listed below:

(1) The intermediate obtained in the asymmetric reaction step of Example 7: Dimethyl (R)-1-diphenylmethylamino-hexylphosphonate $[\alpha]_D$ –168.6° (c=0.7, CHCl$_3$)

$^1$H-NMR(CDCl$_3$): peak values are as follows:

δ: 7.17–7.45(m, 10H), 5.23(s, 1H), 3.79(d, J=10.2 Hz, 3H), 3.74(d, J=10.2 Hz, 3H), 2.80–2.92(m, 1H), 1.13–1.87 (m, 9H), 0.87(t, J=6.9 Hz, 3H);

(2) The intermediate obtained in the asymmetric reaction step of Example 8: Dimethyl (R)-1-diphenylmethylamino-propylphosphonate $[\alpha]_D$ –34.8° (c=1.7, CHCl$_3$)

$^1$H-NMR(CDCl$_3$): peak values are as follows.

δ: 7.38–7.50(m, 4H), 7.14–7.36(m, 6H), 5.20(br s, 1H), 3.80(d, J=10.2 Hz, 3H), 3.74(d, J=10.2 Hz, 3H), 2.84(dt, J=13.9, 6.9 Hz, 1H), 1.72–1.99(m, 2H), 1.60(br s, 1H); 1.02(t, J=6.9 Hz, 3H);

(3) The intermediate obtained in the asymmetric reaction step of Example 9: Dimethyl (S)-1-diphenylmethylamino-2-propylphosphonate;

(4) The intermediates obtained in each asymmetric reaction step of Examples 10 and 11: Dimethyl (R)-(E)-1-diphenylmethylamino-3-phenyl-2-propenylphosphonate $^1$H-NMR(CDCl$_3$): peak values are as follows.

δ: 7.12–7.48(m, 15H), 6.51(dd, J=15.8, 4.0 Hz, 1H), 6.15(ddd, J=15.8, 9.0, 5.9 Hz, 1H), 5.03(s, 1H), 3.89(d, J=10.6 Hz, 3H), 3.76(d, J=10.6 Hz, 3H), 3.64(dd, J=21.0, 9.0 Hz, 1H), 2.17(br s, 1H);

(5) The intermediate obtained in the asymmetric reaction step of Example 12: Dimethyl (R)-1-p-methoxyphenylamino-cyclohexylmethylphosphonate $[\alpha]_D$ +14.9° (c=2.0, CHCl$_3$)

$^1$H-NMR(CDCl$_3$): peak values are as follows.

δ: 6.76(d, J=8.9 Hz, 2H), 6.61(d, J=8.9 Hz, 2H), 3.74(s, 3H), 3.71(d, J=10.6 Hz, 3H), 3.67(d, J=10.6 Hz, 3H), 3.53(dd, J=18.8, 3.6 Hz, 1H), 1.09–2.02(m, 12H);

(6) The intermediate obtained in the asymmetric reaction step of Example 13: Dimethyl (R)-1-diphenylmethylamino-ethylphosphonate $^1$H-NMR(CDCl$_3$): peak values: are as follows.

δ: 7.16–7.45(m, 10H), 5.23(d, 1H), 3.79(d, 3H), 3.74(d, 3H), 2.80–2.92(m, 1H), 1.02–1.04(q, 3H);

(7) The intermediate obtained in the asymmetric reaction step of Example 14: Dimethyl (R)-1-diphenylmethylamino-butylphosphonate $^1$H-NMR(CDCl$_3$): peak values are as follows.

δ: 7.10–7.46(m, 10H), 5.22(d, 1H), 3.78(d, 3H), 3.74(d, 3H), 3.00–3.20(m, 1H), 1.40–2.00(m, 4H), 0.95(t, 3H);

(8) The intermediate obtained in the asymmetric reaction step of Example 15: Dimethyl (R)-1-diphenylmethylamino-butylphosphonate $^1$H-NMR(CDCl$_3$): peak values are as follows.

δ: 7.10–7.53(m, 10H), 5.20(d, 1H), 3.79(d, 3H), 3.72(d, 3H), 2.92–3.05(m, 1H), 1.10–1.90(m, 6H), 0.90(t, 3H);

(9) The intermediate obtained in the asymmetric reaction step of Example 16: Dimethyl (R)-1-diphenylmethylamino-tridecylphosphonate $^1$H-NMR(CDCl$_3$): peak values are as follows.

δ: 7.05–7.50(m, 10H), 5.20(d, 1H), 3.80(d, 3H), 3.74(d, 3H),2.80–2.92(m, 1H), 1.10–2.10(m, 22H), 0.88(t, 3H);

(10) The intermediate obtained in the asymmetric reaction step of Example 17: Dimethyl (R)-1-diphenylmethylamino-3-methylbutylphosphonate $^1$H-NMR(CDCl$_3$): peak values are as follows.

δ: 7.17–7.45(m, 10H), 5.24(d, 1H), 3.78(d, 3H), 3.74(d, 3H), 2.80–2.92(m, 1H), 2.05–2.40(m, 1H), 1.52–1.70(m, 2H), 1.00–1.05(d, 6H);

(11) The intermediate obtained in the asymmetric reaction step of Example 18: Dimethyl (R)-1-diphenylmethylamino-phenylmethylphosphonate $^1$H-NMR(CDCl$_3$): peak values are as follows.

δ: 7.10–7.60(m, 15H), 5.20(d, 1H), 4.50(s, 1H), 3.79(d, 3H), 3.74(d, 3H);

(12) The intermediate obtained in the asymmetric reaction step of Example 19: Dimethyl (R)-1-diphenylmethylamino-p-chlorophenylmethylphosphonate $^1$H-NMR(CDCl$_3$): peak values are as follows.

δ: 7.10–7.75(m, 14H), 5.25(d, 1H), 4.30(s, 1H), 3.75(d, 3H), 3.70(d, 3H);

(13) The intermediate obtained in the asymmetric reaction step of Example 20: Dimethyl (R)-1-diphenylmethylamino-p-fluorophenylmethylphosphonate $^1$H-NMR(CDCl$_3$): peak values are as follows.

δ: 7.05–7.60(m, 14H), 5.23(d, 1H), 4.50(s, 1H), 3.75(d, 3H), 3.70(d, 3H);

(14) The intermediate obtained in the asymmetric reaction step of Example 21: Dimethyl (R)-1-diphenylmethylamino-p-methoxyphenylmethylphosphonate $^1$H-NMR(CDCl$_3$): peak values are as follows.

δ: 7.10–7.70(m, 14H), 5.20(d, 1H), 4.50(s, 1H), 3.85(d, 3H),3.75(d, 3H), 3.68(d, 3H); and

(15) The intermediate obtained in the asymmetric reaction step of Example 22: Dimethyl (R)-1-diphenylmethylamino-2-phenylethylphosphonate $^1$H-NMR(CDCl$_3$): peak values are as follows.

δ: 7.11–7.55(m, 15H), 5.20(d, 1H), 3.80(d, 3H), 3.75(d, 3H), 3.15–3.37(m, 2H), 2.80–2.92(m, 1H).

Industrial Utilizablity

The process of the first aspect of this invention can prepare via a few reaction steps an (R)- or (S)-1- aminophosphonic acid derivative having a high percentage of enantiometric excess in a high yield, by reacting prochiral starting compounds in the presence of an asymmetric catalyst. The (R)- or (S)-1-aminophosphonic acid derivative so prepared by the process is useful itself as a pharmaceutics or is useful as a starting materials available for the productions of pharmaceutics or agricultural chemicals. Furthermore, the process of the second aspect of this invention can prepare the asymmetric catalyst for use in the process of the first aspect of this invention.

We claim:

1. A process for the preparation of an optically active (R)- or (S)-1-aminophosphonic acid derivative represented by the general formula (Ia) or (Ib):

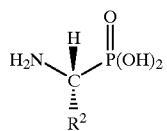
(Ia)

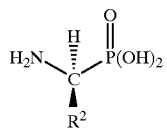
(Ib)

wherein R² has the same meaning as given below, characterized in that the process comprises the following steps:

reacting an imine represented by the general formula (II):

(II)

wherein R¹ stands for diphenylmethyl group or an alkoxyphenyl group and R² stands for an alkyl group or a cycloalkyl group, or an aryl group-containing hydrocarbon radical, or R² stands for an aryl group optionally substituted with a halogen atom or an alkoxy group, with a phosphonic acid ester represented by the general formula (III):

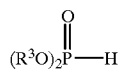
(III)

wherein R³ stands for an alkyl group, a cycloalkyl group, allyl group or an aryl group or an aryl group-containing hydrocarbon radical, in the presence of an asymmetric catalyst consisting of a rare earth element-alkali metal-binaphthol complex to produce a (R)- or (S)-N-protected-1-aminophosphonate compound represented by the general formula (IVa) or (IVb):

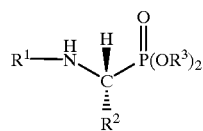
(IVa)

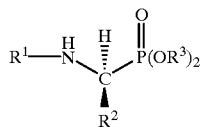
(IVb)

wherein R¹, R² and R³ have the same meanings as defined above;

subjecting the compound of the formula (IVa) or (IVb) to catalytic reduction with hydrogen to eliminate the amino-protecting group R¹ therefrom to produce a (R)- or (S)-1-aminophosphonic acid ester represented by the formula (Ia') or (Ib'):

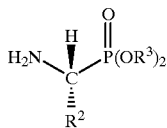
(Ia')

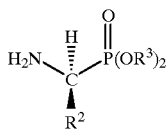
(Ib')

wherein R³ has the same meaning as defined above; and subjecting the resulting compound of the formula (Ia') or (Ib') to acidic hydrolysis to eliminate the ester-forming group R³ therefrom.

2. A process for the preparation of a compound of the formula (Ia) or (Ib) as claimed in claim 1, characterized in that a compound of the formula (IVa) or (IVb) is directly contacted with an acid to deprotect the N-protected amino group of the compound of the formula (IVa) or (IVb) and to hydrolyze the group OR³ of the latter compound, whereby the compound of the formula (Ia) or (Ib) is produced.

3. A process according to claim 1, wherein the asymmetric catalyst used is such a complex of a rare earth element with an alkali metal and (R)-(+)-1,1'-bi-2-naphthol or (S)-(−)-1,1'-bi-2-naphthol, which has been prepared by a method comprising reacting in an anhydrous organic solvent or aqueous organic solvent (R)-2,2'-dihydroxy-1,1'-binaphthyl, namely (R)-(+)-1,1'-bi-2-naphthol of the formula (V$_R$):

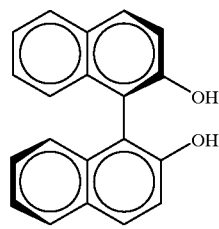
(V$_R$)

or (S)-2,2'-dihydroxy-1,1'-binaphthyl, namely (S)-(−)-1,1'-bi-2-naphthol of the formula (V$_S$):

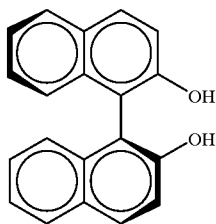 (V_S)

with a rare earth element alkoxide of the formula (VI):

$$Ln(OR)_3 \quad (VI)$$

wherein Ln stands for a rare earth element and R stands for a ($C_1$–$C_4$)-alkyl group; and an alkali metal compound selected from the group consisting of an alkyl lithium of the general formula (VII):

$$LiR \quad (VII)$$

wherein R stands for a ($C_1$–$C_4$)-alkyl group; and trimethylsilyl potassium amide of the general formula (VIII):

$$[(CH_3)_3Si]_2NK \quad (VIII)$$

and an alkali metal alkoxide of the general formula (IX):

$$Z(OR) \quad (IX)$$

wherein Z stands for an alkali metal and R stands for a ($C_1$–$C_4$)-alkyl group, in such proportions of these reactant compounds that the molar ratio between the compound of the formula ($V_R$) or ($V_S$), the rare earth element alkoxide of formula (VI) and the alkali metal compound of the formula (VII), (VIII) or (IX) is in a range of 1~10:1:1~10, at a temperature of 0 to 50° C. but at a temperature of not higher than the boiling point of the solvent used, for 0.1 to 100 hours under the atmosphere of an inactive gas, thereby to produce said complex and then collecting from the resulting reaction solution the complex as the catalyst for the asymmetric synthesis.

* * * * *